United States Patent
Yamamoto

(10) Patent No.: US 9,138,660 B2
(45) Date of Patent: Sep. 22, 2015

(54) METHOD FOR REDUCING WATER CONTENT OF AN OBJECT TO BE TREATED

(75) Inventor: Masahiro Yamamoto, Kagoshima (JP)

(73) Assignees: Masahiro Yamamoto, Kagoshima (JP); Kirishima Highland Beer Co., Ltd., Kagoshima (JP)

( * ) Notice: Subject to any disclaimer, the term of this patent is extended or adjusted under 35 U.S.C. 154(b) by 171 days.

(21) Appl. No.: 14/119,123

(22) PCT Filed: May 7, 2012

(86) PCT No.: PCT/JP2012/061637
§ 371 (c)(1),
(2), (4) Date: Nov. 20, 2013

(87) PCT Pub. No.: WO2012/160955
PCT Pub. Date: Nov. 29, 2012

(65) Prior Publication Data
US 2014/0102157 A1    Apr. 17, 2014

(30) Foreign Application Priority Data
May 25, 2011    (JP) .................................. 2011-117189

(51) Int. Cl.
*F26B 21/00*    (2006.01)
*B01D 11/00*    (2006.01)
(Continued)

(52) U.S. Cl.
CPC . *B01D 11/00* (2013.01); *A23F 3/16* (2013.01); *A23K 1/00* (2013.01); *A23L 1/36* (2013.01);
(Continued)

(58) Field of Classification Search
CPC .......... F26B 11/00; F26B 19/00; F26B 21/00; A23K 1/00; A23K 1/06; A23K 1/10; A23K 1/14

USPC ............ 34/381, 407, 413, 497; 210/631, 638, 210/642; 426/429
See application file for complete search history.

(56) References Cited

U.S. PATENT DOCUMENTS 6,184,193 B1 *    2/2001    Yamada ........................ 510/291
6,703,054 B2 *    3/2004    Yamamoto ...................... 426/7
(Continued)

FOREIGN PATENT DOCUMENTS

| CA | 1-215-932 A1 | 12/1986 |
| GB | 190429137 | * 0/1904 |

(Continued)

OTHER PUBLICATIONS

EPO Communication pursuant to Rule 164(1) EPC, with a partial Supplementary European Search Report, dated Jan. 21, 2015, issued by the European Patent Office, Munich, Germany, in corresponding European Patent Application No. EP 12788805.5 (7 pages).
(Continued)

*Primary Examiner* — Stephen M Gravini
(74) *Attorney, Agent, or Firm* — Osha Liang LLP

(57) ABSTRACT

A method for efficiently reducing water content of an object to be treated that contains water without requiring a high-temperature environment such as one exceeding the boiling point of water, and a method for efficiently extracting an oil-soluble substance from an object to be treated that contains water and the oil-soluble substance. A method for reducing water content of an object to be treated and/or extracting an oil-soluble substance in the object to be treated into oil is performed by mixing the object to be treated containing water or water and the oil-soluble substance with an oil at a temperature that is lower than the boiling point of water, at which temperature the oil is a liquid.

25 Claims, 1 Drawing Sheet

(51) Int. Cl.

| | |
|---|---|
| *C05G 3/00* | (2006.01) |
| *B01D 1/20* | (2006.01) |
| *C10G 33/06* | (2006.01) |
| *F26B 5/00* | (2006.01) |
| *F23G 5/04* | (2006.01) |
| *F23G 7/00* | (2006.01) |
| *A23F 3/16* | (2006.01) |
| *A23K 1/00* | (2006.01) |
| *A23L 1/36* | (2006.01) |
| *C02F 1/26* | (2006.01) |
| *C05F 11/00* | (2006.01) |
| *C07C 51/48* | (2006.01) |
| *C12H 1/00* | (2006.01) |
| *C02F 1/04* | (2006.01) |
| *C02F 11/12* | (2006.01) |
| *C10G 32/00* | (2006.01) |
| *C10G 33/00* | (2006.01) |
| *C10G 1/00* | (2006.01) |
| *C10G 1/04* | (2006.01) |
| *B01D 1/18* | (2006.01) |
| *B01D 12/00* | (2006.01) |

(52) U.S. Cl.
CPC .. *B01D 1/18* (2013.01); *B01D 1/20* (2013.01); *B01D 12/00* (2013.01); *C02F 1/048* (2013.01); *C02F 1/265* (2013.01); *C02F 11/12* (2013.01); *C05F 11/00* (2013.01); *C05G 3/007* (2013.01); *C07C 51/48* (2013.01); *C10G 1/002* (2013.01); *C10G 1/04* (2013.01); *C10G 32/00* (2013.01); *C10G 33/00* (2013.01); *C10G 33/06* (2013.01); *C12H 1/00* (2013.01); *F23G 5/04* (2013.01); *F23G 7/001* (2013.01); *F26B 5/005* (2013.01); *Y02W 30/43* (2015.05)

(56) References Cited

U.S. PATENT DOCUMENTS

| | | | | |
|---|---|---|---|---|
| 8,359,765 | B2* | 1/2013 | Doll et al. | 34/59 |
| 8,407,916 | B2* | 4/2013 | Haerle et al. | 34/381 |
| 2003/0012847 | A1 | 1/2003 | Yamamoto | |
| 2004/0187340 | A1* | 9/2004 | Chemat et al. | 34/259 |
| 2005/0120715 | A1* | 6/2005 | Labrador | 60/618 |
| 2007/0027036 | A1* | 2/2007 | Polizzotti et al. | 507/143 |
| 2008/0064075 | A1* | 3/2008 | Yamamoto | 435/161 |
| 2010/0212180 | A1* | 8/2010 | Munter et al. | 34/386 |
| 2010/0320126 | A1* | 12/2010 | Wu | 208/48 R |
| 2012/0214219 | A1* | 8/2012 | Aines et al. | 435/174 |
| 2014/0299529 | A1* | 10/2014 | Govind et al. | 210/195.2 |

FOREIGN PATENT DOCUMENTS

| | | | |
|---|---|---|---|
| JP | S53-144874 | A | 12/1978 |
| JP | 2002-121019 | A | 4/2002 |
| JP | 2002-205026 | A | 7/2002 |
| JP | 2003-235464 | A | 8/2003 |
| JP | 2004-148253 | A | 5/2004 |
| JP | 2005-081262 | A | 3/2005 |
| JP | 2007-181774 | A | 7/2007 |
| JP | 2008-188520 | A | 8/2008 |
| JP | 2009-007563 | A | 1/2009 |
| JP | 2011-005471 | A | 1/2011 |
| KR | 101198143 | * | 6/2012 |
| WO | WO 2012099778 A8 | * | 9/2012 |

OTHER PUBLICATIONS

PCT Notification of Transmittal of Translation of The International Preliminary Report on Patentability, with an English translation of the PCT International Preliminary Report on Patentability mailed Nov. 28, 2013, by The International Bureau of WIPO, Geneva, Switzerland (5 pages).

International Search Report for corresponding International Application No. PCT/JP2012/061637, mailed Aug. 7, 2012 (8 pages).

* cited by examiner

METHOD FOR REDUCING WATER CONTENT OF AN OBJECT TO BE TREATED

CROSS-REFERENCE TO RELATED APPLICATIONS

This is a national stage application based on PCT/JP2012/061637, filed on May 7, 2012, which claims priority to Japanese Patent Application No. 2011-0117189, filed on May 25, 2011. This application claims the priority of these prior applications and incorporates their disclosures by reference in their entireties.

TECHNICAL FIELD

The present invention relates to (1) a method for reducing water content of an object to be treated or increasing solute concentration of an aqueous solution by mixing a water-containing substance (for example, a water-containing waste such as sludge generated by sewage treatment, livestock excreta, or the like; a residue by beverage or food manufacturing such as a water-containing food (e.g., vegetables), sediment from tea, or the like; an effluent of Shochu (a distilled spirit) production, grain, a dead fish, garbage of a fish, kitchen garbage, or water-containing feed derived from, as a raw material, an effluent of Shochu production, grain, a dead fish, garbage of a fish, or kitchen garbage; an effluent of palm oil production; blood; or the like); an aqueous solution such as sea water or the like; or a concentrate of the water-containing substance or the aqueous solution, which is an object to be treated, with oil at a temperature that is lower than the boiling point of water, such as an ordinary temperature or the like, and (2) a method for extracting an oil-soluble substance in an object to be treated into an oil by mixing a water-containing substance that comprises the oil-soluble substance (e.g., hydrous tea-leaf, grinded nut of palm, or grinded nut of camellia), which is the object to be treated, with oil at a temperature that is lower than the boiling point of water, such as an ordinary temperature or the like.

BACKGROUND ART

Water-containing substances, such as kitchen garbage, residue by food manufacturing, an effluent of Shochu production, an effluent of palm oil production, livestock excreta, sludge generated by sewage treatment and the like, have high water content. Thus, it is difficult to directly incinerate them. Heretofore, many studies and proposals have been performed about the use of these water-containing substances by reducing the volume of them (i.e., drying them to reduce their volume) and then using them as an organic waste fuel as they are or after mixing with oil, and about the recycling of the water-containing substances as livestock feed or fertilizer by applying fermentation techniques.

Patent literature 1 discloses a method for treating food residue characterized by adding to the food residue a dispersant such as a surfactant, an antifoamer, a flocculant, a fat and oil, or the like, mixing, and drying by heat. The treated object thus obtained is, for example, in a powdery or granular state, and is used as feed or diet, or as a raw material for producing fertilizer.

Patent literature 2 discloses a method for producing an organic waste fuel which comprises steps of performing methane fermentation of an organic waste such as food waste or the like, mixing the residue of the methane fermentation thus obtained with waste oil, and heating the obtained mixture under condition of a reduced pressure at a constant temperature (70 to 100 degrees Celsius). The water content of the organic waste fuel obtained by this method is from 20 to 40%.

Patent literature 3 discloses a method for producing feed which comprises steps of adding Koji-kin (fungi belong to *Aspergillus*) or rice malt, and an oil and fat to an organic waste such as kitchen garbage or the like, and fermenting the organic waste with the Koji-kin to remove water in the organic waste by evaporation.

Patent literature 4 discloses a method for treating biomass, which comprises fermenting biomass such as dehydrated cake of sludge generated by sewage treatment, or the like, to produce an acid, dehydrating the obtained biomass in oil under certain conditions of temperature and pressure (for example, at a temperature of about 150 degrees Celsius under a pressurized condition of about 0.3 MPa), under which conditions the acid evaporates, to obtain a mixture of the oil with a dry biomass and vapor containing the acid, deoiling the mixture to obtain the dry biomass, and condensing the vapor containing the acid to obtain an acid-containing water.

Patent literature 5 discloses a device of circulation type for dry-treatment at ordinary temperature employing a repeating system, one cycle of which comprises heating organic substances such as food waste or the like at a temperature within an ordinary range in a treatment tank while agitating the organic substances, having air holding water that is contained in the organic substances as water vapor to bring the water vapor out of the treatment tank, condensing the water vapor by a condenser that is separately arranged to remove water, and returning the air, from which water has been removed, to the treatment tank. Although the drying method by using this device does not use an oil and fat, patent literature 5 discloses that the drying temperature may be several degrees Celsius higher than that in the treatment tank, and that heating may be performed by a heater to be about 37 degrees Celsius if the temperature in the treatment tank is, e.g., about 30 degrees Celsius in a summer season.

PRIOR-ART LITERATURES

Patent Literatures

Patent literature 1: Japanese Patent Laid-open No. 2002-205026

Patent literature 2: Japanese Patent Laid-open No. 2009-7563

Patent literature 3: Japanese Patent Laid-open No. 2003-235464

Patent literature 4: Japanese Patent Laid-open Open No. 2007-181774

Patent literature 5: Japanese Patent Laid-open No. 2011-5471

BRIEF DESCRIPTION OF INVENTION

Problem to be Solved by Invention

In the conventional drying methods that use oil as disclosed in patent literatures 1 to 4, water-containing substances were dried by means of, e.g., drying by heat or drying by fermentation. However, in the drying by heat, the latent heat of vaporization per one liter of water is about 700 kcal, and thus we have to depend on heat energy by combustion of fossil fuel. Further, since the combustion of fossil fuel generates carbon dioxide, it is contributory to global warming phenomena, too. Moreover, in the case where the heating temperature is high, a harmful substance was sometimes generated, or it sometimes became difficult to agitate the water-containing substance or evaporate water because the viscosity of the water-containing substance increases by the polymerization of a certain component in that substance. Contrary, in the case where the heating temperature is low (for example, in the case of drying within a range of ordinary temperatures), there were defects that the water content did not come to be sufficiently low and that it took a great deal of time to dry the water-containing substance.

Drying by fermentation is that a mixture of a water-containing substance and microorganism is warmed by heat of fermentation of the microorganism and that a gas is blown to the mixture so that latent heat of vaporization is drawn. Although this method does not use fossil fuel for warming, there were defects that the fermentation conditions had to be controlled depending on the kind of the water-containing substance to be treated and that it took a great deal of time to dry the water-containing substance. The method of patent literature 5 does not use an oil and fat. By the method only the surface of the organic substance is dried. Therefore, although the organic substance is agitated, despite this, the drying efficiency is low.

The purpose of this invention is to solve conventional problems in drying of a water-containing substance, namely, to provide a method for efficiently reducing water content of an object to be treated that contains water, without requiring a high-temperature environment such as one exceeding the boiling point of water. Also, the purpose of this invention is to provide a method for efficiently extracting an oil-soluble substance from an object to be treated that contains water and the oil-soluble substance, which method comprises similar treatment steps to those of the above method for efficiently reducing water content.

Means for Solving Problem

Namely, the present invention relates to a method for reducing water content of an object to be treated characterized in that the object to be treated containing water or water and an oil-soluble substance, and liquid oil are prepared in such a ratio that the amount of the object to be treated is 60% by weight or lower of that of the oil, and they are mixed under ordinary pressure at a temperature of 20 to 45 degrees Celsius.

The mixing of the object to be treated with the oil in the above method can be specifically performed by the following methods:

(1) the mixing of the object to be treated with the oil is performed by using a cooling tower, supplying the object to be treated and the oil into a storage tank that is set at a lower part of the cooling tower, transporting the object to be treated and the oil from the storage tank to an upper part of the cooling tower, and showering down them from the upper part of the cooling tower to the storage tank, preferably showering down at least a part of the object to be treated and the oil that have been transported to the upper part of the cooling tower to the storage tank through a loading material.

(2) the mixing of the object to be treated with the oil is performed by installing a submersible pump in a storage tank, impounding the object to be treated and the oil in the storage tank, and spraying a fountain of them by using the submersible pump.

(3) the mixing of the object to be treated with the oil is performed by bubbling a mixture of the object to be treated and the oil with a gas, and/or, stirring the mixture.

(4) the mixing of the object to be treated with the oil is performed by shaking or vibrating a container in which the mixture is contained.

The mixing of the object to be treated with the oil may be performed until the water content of the object comes to be a predetermined value. Here, the "predetermined value" is specified depending on the intended use of a concentrate of the object to be treated or a dry substance. By performing the method of the present invention, it is also possible to attain the water content of substantially 0%.

A gas may be blown, for example, on or above the mixture of the object to be treated and the oil so that the gas comes into contact with the mixture.

The gas that may be used for bubbling or that may be blown is, for example, air, carbon dioxide, nitrogen, or the like. The gas is preferably dry one having a low water content.

In the case where the gas is blown on or above a mixture of the object to be treated and the oil, it may be constituted so that the gas passes through only once on or above the mixture of the object to be treated and the oil. Or, the gas may be used in circle, wherein the gas that has held water by passing through on or above the mixture of the object to be treated and the oil is dried (for example, the water is removed from the gas in a condenser) and then is again used for passing through on or above the mixture.

In addition to the object to be treated and the oil, a cationic or anionic surfactant may be used.

In the case where, e.g., the oil that has been used for treatment is intended to be used, the method of the present invention may be performed in the presence of at least one microorganism selected from the group consisting of various Koji-kin, Phizopus, and Mucor or in the presence of an anti-oxidative substance. In the case where the microorganism is used, it is preferably to perform the method at a temperature equal to or lower than the upper temperature limit of the microorganism.

Further, the present invention relates to a method for producing fuel, which comprises a step (1) for reducing water content of an object to be treated by preparing the object to be treated containing water or water and an oil-soluble substance, and liquid oil in such a ratio that the amount of the object to be treated is 60% by weight or lower of that of the oil, and mixing them under ordinary pressure at a temperature of 20 to 45 degrees Celsius, and a step (2) for molding a mixture of the treated object, of which water content has been reduced, and the oil. The molding is performed by, e.g., extruding the above mixture by using an extruder.

Furthermore, the present invention relates to a method for producing feed, diet, or fertilizer, which comprises a step (a step (1)) for reducing water content of an object to be treated by preparing the object to be treated containing water or water and an oil-soluble substance, and liquid oil in such a ratio that the amount of the object to be treated is 60% by weight or lower of that of the oil, and mixing them under ordinary pressure at a temperature of 20 to 45 degrees Celsius. The water content at the completion of the step (1) may be an intended value, depending on the property that is required for the product that is obtained by performing the step (1). For example, if an additional treatment is performed after the step (1), the step (1) may be performed so that an intended water content is attained at the completion of the step (1), wherein the intended water content depends on a specific treatment method that is performed after the step (1) or the property that is required in a final product. After the step (1), a step (a step (2)) may be performed for separating from the oil the treated object, of which water content has been reduced.

In the method for producing feed, diet, or fertilizer according to the present invention, the feed, the diet, or the fertilizer may be produced by using the mixture as is of the treated object, of which water content has been reduced, and the oil that has been used in the treatment after the completion of the step (1). Or, the feed, the diet, or the fertilizer may be produced by performing the step (2) by a method of, e.g., separating the treated object, of which water content has been reduced, from the oil that has been used in the treatment, and then using the treated and separated object. In the case where the step (2) is performed, at need, part or all of the oil that contaminates the treated and separated object may be removed.

Furthermore, the present invention relates to a method for producing a dry substance derived from a concentrate of an object to be treated or the object to be treated, which comprises a step (1) for reducing water content of the object to be treated by preparing the object to be treated containing water or water and an oil-soluble substance, and liquid oil in such a ratio that the amount of the object to be treated is 60% by weight or lower of that of the oil, and mixing them under ordinary pressure at a temperature of 20 to 45 degrees Celsius, and a step (2) for separating from the oil the treated object, of which water content has been reduced.

In the above method for producing a dry substance derived from a concentrate of an object to be treated or the object to be treated, the separation of other component from the oil may be performed, e.g., as follows. In the case where the concentrated object is still liquid, the liquid is separated into an oil phase and an aqueous phase by leaving the liquid to stand or by centrifugation, and after separation the aqueous phase as the lower layer is tapped off so that the oil phase does not contaminate the aqueous phase.

In the case where the step (1) is performed until substantially no water remains in a treated object, the treated object containing substantially no water can be obtained by taking off the treated object containing substantially no water (step (2)), and then performing a step (3) for washing the treated object with a solvent that can dissolve and clean up the oil, and a step (4) for removing the solvent that was used for washing. In this case centrifugation may be performed as a part (a first half) of the step (2). Further, the oil content of the treated object may be reduced by compressing the treated object that was taken off, instead of the steps (3) and (4).

Further, also in the case where the step (1) is discontinued at a condition that the treated object contains a certain amount (namely, an amount that is suitable for the next step) of water, the oil content of the treated object may be reduced by taking off the treated object, of which water content has been reduced (step (2)), and then (3) compressing the treated object, of which water content has been reduced. In this case centrifugation may be performed as a part (a first half) of the step (2).

A method for producing a dry substance derived from an object to be treated is also a method of the present invention, which comprises, in this order, a step (I) for reducing water content of the object to be treated by mixing the object to be treated containing water or water and the oil-soluble substance with oil at a temperature that is lower than the boiling point of water at which temperature the oil is liquid, a step (II) for separating from the oil the treated object, of which water content has been reduced, and a step (III) for compressing the treated object, of which water content has been reduced, to reduce oil content of the treated object, and further comprises, after the step (II) or (III), a step (IV) for adding microorganism to the treated object, of which water content has been reduced, and fermenting it to obtain fermented feed, fermented diet, or fermented fertilizer.

Furthermore, the present invention also relates to a method for obtaining fresh water from sea water, which comprises (i) mixing the sea water or a concentrate of it with oil at a temperature that is lower than the boiling point of water, at which temperature the oil is liquid, (ii) during the above mixing, blowing a gas so that the gas comes into contact with the mixture of the sea water or the concentrate of it and the oil to make the gas hold the water that is derived from the sea water or the concentrate of it, and (iii) removing the water from the gas that has held the water. In this method, by blowing the gas, from which the water has been removed in step (iii), to the step (ii), the gas can be used in circles.

Moreover, the present invention also relates to a method for extracting an oil-soluble substance in an object to be treated into oil, which comprises a step (1) for extracting the oil-soluble substance in the object to be treated into the oil by mixing the object to be treated containing water or water and the oil-soluble substance with the oil at a temperature that is lower than the boiling point of water, at which temperature the oil is liquid, and a step (2) for separating from the oil the treated object, from which the oil-soluble substance has been extracted.

Effect of Invention

By the present invention, it becomes possible to efficiently reduce water content of an object to be treated that contains water so that the water content comes to be preferably 0% or next to 0%, without requiring a high-temperature environment. In the case where the object to be treated is an aqueous solution, reduction of the water content means increase of the concentration of solute.

The method of the present invention can be applied to reduce volume of an organic waste. By the present invention, volume reduction of waste (garbage) can be attained.

By the method of the present invention, fuel of organic waste can be obtained, of which water content is low and of which calorie is high. Further, by the method of the present invention, feed or diet for livestock or fishes, or fertilizer can be obtained, wherein because the water content of the feed or diet, or the fertilizer is low, it is difficultly gone moldy. When the production of the feed or diet is performed at a lower temperature, deterioration in quality by thermal denaturation does not arise. If part or all of the oil that has been used in the treatment for reducing water content is left in the feed or diet, feed or diet having high calorie can be obtained.

The method of the present invention can also be applied to concentration of sea water or a production of salt from sea water. This means that in the concentration of sea water or the production of salt from sea water, choices of a method that can be employed increase. Further, during the concentration of sea water or the production of salt from sea water, water vapor derived from sea water can be obtained. By condensing the water vapor, fresh water can be obtained. Thus, by the present invention, choices of a method that can be employed also increase in the production of fresh water from sea water.

The method of the present invention can also be applied to the extraction into oil of an oil-soluble substance in an object to be treated. By this method, efficient extraction of an oil-soluble and useful substance can be attained. Further, by concurrently using at least one microorganism selected from the group consisting of various Koji-kin, Phizopus, and Mucor or an antioxidative substance, oil containing an oil-soluble and useful substance and having high quality can be obtained because the oxidation of oil is inhibited.

Furthermore, by treating an object to be treated such as livestock excreta, a dead fish, garbage of a fish, or the like by the method of the present invention, with the proviso that the above microorganism is concurrently used, environmental pollution based on bad odor can be solved, because the odor of the object to be treated is drastically reduced by the treatment.

If the method of the present invention is performed without heating, energy cost can be drastically reduced.

MODE FOR PERFORMING INVENTION

Figure 1:
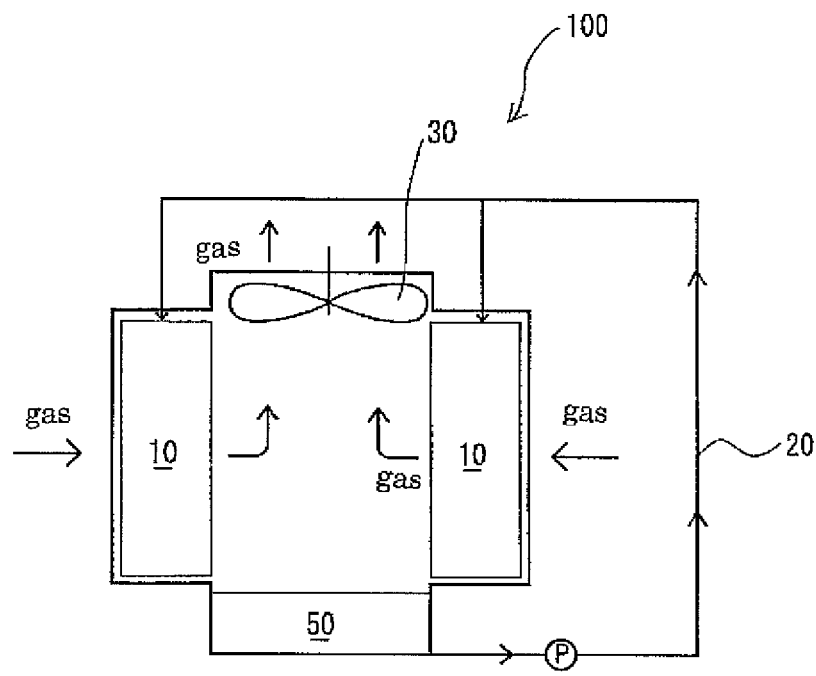
FIG. 1 is a schematic and diagrammatic view of vertical section of an example of a cooling tower.

In the present invention, the wording "an object to be treated" means an organic or inorganic substance containing water as an essential component. Although usually the water is originally contained in the object to be treated, it may be added one. The "object to be treated" may be one further comprising an oil-soluble substance. The wording "an oil-soluble substance" means one that is dissolved in and extracted into oil that was used for mixing, when the method of the present invention was performed. The organic or inorganic substance may be comprised of one type only or a mixture of two or more types. The object to be treated may be in the form of a mixture of a solid substance and liquid (for example, a solid substance absorbing water, a mixture of water and a solid substance absorbing water, or a mixture of a solid substance, an aqueous liquid, and an oily fluid), or an aqueous solution of an organic or inorganic substance.

Examples of the mixture of a solid substance and liquid among objects to be treated include water-containing wastes such as kitchen garbage, a residue by food manufacturing (specifically, residues of vegetables, fruits, dead fishes, fish meats, meats of livestock, and the like; Okara (soy pulp), rice bran, and sediment from tea), blood, bagasse, an effluent of Shochu production, a residue after pressing Shochu, residue after pressing Sake (rice wine) lees, an effluent of wine production, an effluent of beer production, beer lees, an effluent of whisky production, a residue after coffer extraction, an effluent of palm oil production, livestock excreta, dead fishes, garbage of a fish, sludge derived from sewage, and the like; hydrous tea-leaf; grinded nut of palm; grinded nut of camellia; and the like. Examples of objects to be treated in the form of an aqueous solution include sea water, a concentrate of the sea water, and the like.

The oil that is used in the present invention is liquid at the temperature where the method of the present invention is performed. Usually, oil that is liquid at an ordinary temperature is used. The oil may be one that comprises water. Specific examples of the oil include various vegetable oils, waste oils of edible oils such as cooking oil for Tenpura (a mixture of vegetable oils), and the like; waste oils of fuel oils discharged from factories, waste engine oil, waste lubricating oil for turbine, waste glycerol, and the like. Depending on the use of the treated object, the kind of the oil to be used may be restricted. For example, when a treated object that has been obtained by providing an object to be treated to the method of the present invention is used as a raw material for feed or diet, or when a concentrate (an aqueous phase) or a dry substance obtained is food such as sea water, salt, or the like, edible oils such as various vegetable oils or waste oils of the edible oils are used. When a treated object that has been obtained by providing an object to be treated to the method of the present invention is used as a fuel, the oil is preferably waste oil of fuel oil discharged from a factory, waste engine oil, waste lubricating oil for turbine, waste glycerol, or the like. When an obtained oil phase is used after an object to be treated was provided to the method of the present invention, oil is selected depending on the use of the oil phase.

A mixing ratio of the object to be treated and the oil is not particularly limited. However, usually, the object to be treated≤the oil, and preferably the amount of the object to be treated is 60% by weight or less of that of the oil.

Mixing of the object to be treated with the oil is performed at a temperature that is lower than the boiling point of water. The reason why the temperature is specified "at a temperature that is lower than the boiling point of water" is that the method of the present invention can be performed under reduced or increased pressure, as well as under ordinary pressure. The "temperature that is lower than the boiling point of water" means less than 100 degrees Celsius under ordinary pressure. Under ordinary pressure, it is preferable to perform the mixing of the object to be treated with the oil at a temperature that is equal to or higher than the melting point of the oil to be used and is 80 degrees Celsius or lower. However, it may be performed at a temperature that is equal to or higher than 5 degrees Celsius plus the melting point of the oil to be used and is 70 degrees Celsius or lower, at a temperature of 20 to 60 degrees Celsius, or at a temperature of 25 to 50 degrees Celsius. It is also possible to perform it at a temperature of 30 to 45 degrees Celsius. In the case where the mixing is performed at a lower temperature, a risk that a certain component in the object to be treated turns into a harmful substance or polymerizes comes to be very low. If a component that is contained in the object to be treated polymerizes, not only that the efficiency of the reduction of water content is reduced, but it sometimes becomes difficult to attain the water content of substantially 0% by weight.

Although it will be explained in detail later, the method of the present invention is sometimes performed in the presence of microorganism that shows an effect of preventing oxidation of oil. In such a case, the temperature during the mixing of the object to be treated and the oil is preferably equal to or lower than an upper temperature limit of the microorganism.

The mixing of the object to be treated and the oil is performed so as to bring water in the object to be treated into contact with a gas and have the gas hold the water. Specifically, the object to be treated is mixed with the oil by means of bubbling a mixture of the object to be treated and the oil with a gas, stirring the mixture, shaking or vibrating a container in which the mixture is contained, or the like. In the bubbling the more a supply of gas, the higher the efficiency of the reduction of water content of the object to be treated. Thus, it is preferable to provide the gas in state of bubbles in an amount of 100 to 2,000% by volume of the total of the object to be treated and the oil per one minute. Also, it is preferable that the volume of each bubble is smaller. The stirring speed is preferably, e.g., 100 to 10,000 rpm, although it depends on the viscosity of the mixture of the object to be treated and the oil.

The gas is specifically restricted as long as it is innocuous. Thus, from the view point of cost, air is preferable. However, from the view point that the gas does not oxidize the oil, nitrogen or carbon dioxide is preferable. Since the water in the object to be treated is held by the gas, dry gas is preferable.

It is thought that during the mixing of the object to be treated with the oil, the mixture is in an emulsified state, namely, usually in a state that water (an inner phase) derived from the object to be treated is dispersed in the oil (an outer phase). However, this emulsified state is temporary and labile. If there consists of water and oil, the emulsified state is lost by terminating a mixing operation such as stirring, bubbling, or the like. Also, when the water in the object to be treated is gone, the emulsified state is lost. Thus, there was a labile emulsified state during mixing.

During mixing, entirety of the mixture of the object to be treated and the oil is not necessarily in an emulsified state. In some case, only part of the mixture is in an emulsified state.

In the case where a component that shows surface-active property contaminates the oil or the object to be treated that was used, or in the other case where a surfactant is added for performing the method of the present invention as will be described later, the mixture may not separate into an aqueous phase and an oil phase just after the termination of the mixing operation in some cases. Also in those cases, if the mixture separates into an aqueous phase and an oil phase after it was left to stand for a certain period of time, it is determined that it was in "a labile emulsified state" during mixing. For example, an oil to be used and water instead of an object to be treated are prepared, a surfactant to be used is added to the oil and water in an amount that is to be used, mixing is performed for 24 hours, the separating state is observed at 24 hours after the termination of the mixing, and it is determined whether the mixture was in "a labile emulsified state" during mixing. The amount of water that is used instead of the object to be treated (the ratio against the amount of the oil) is one corresponding to the amount of water that is derived from the object to be treated that is to be used (the ratio between the oil and the object to be treated in performing the method of the present invention has been preliminarily decided, and the amount of water that is derived from the object to be treated in the above ratio is calculated). The decision is performed by drawing the separated lower phase (aqueous phase) at 24 hours after the termination of the mixing and determining transmittance of the separated lower phase at a wave length (for example, a wave length of 660 nm), at which wave length the transmittance is unsusceptible by coloration. If the transmittance on this occasion is 20% or above, it can be understood that it was in a labile emulsified state during mixing. It is preferable to perform the method of the present invention under a condition that the transmittance on this occasion is 50% or above, it is more preferable to perform the method of the present invention under a condition that the transmittance is 70% or above, and it is particularly preferable to perform the method of the present invention under a condition that the transmittance is 90% or above. An embodiment in which the oil phase and the aqueous phase separate into two layers comprising an upper layer and a lower layer just after the stopping of the mixing is decided to be "a labile emulsified state" without determining the transmittance by the above method.

The surface of the mixture of the object to be treated and the oil is exposed to a gas. For example, in the case where bubbling is performed for mixing, the bubbles that are formed during the mixing come out from the surface of the mixture. And the surface of the mixture is exposed to a gas (generally air) that always exists around the mixture and another gas derived from the bubbles. If only a stirring is performed, the surface of the mixture is exposed to a gas (generally air) that always exists around the mixture. To more efficiently remove water that is derived from the object to be treated, it may be possible to blow a gas on or above a mixture of the object to be treated and the oil. The gas blown may pass through only once on or above the mixture of the object to be treated and the oil. Or, the gas may be used in circle. The gas absorbs water each time of passing through on or above the mixture of the object to be treated and the oil. Thus, if the gas is used in circle, a constitution is preferable, in which constitution the gas that has been passed on or above the mixture of the object to be treated and the oil is sent to a condenser, and water is removed, namely, the gas is dried, in the condenser.

In the mixing of the object to be treated and the oil, a cationic or anionic surfactant may be coexisted. The type and amount of the cationic or anionic surfactant that is used are those such that the "labile emulsified state" described above is realized. Nonionic and amphoteric surfactants are not preferable because they often form "a stable emulsified state."

Examples of the cationic surfactant include alkyltrimethylammonium chlorides such as lauryltrimethylammonium chloride, stearyltrimethylammonium chloride, cetyltrimethylammonium chloride and the like; dialkyldimethylammonium chlorides such as distearyldimethylammonium chloride and the like; alkyldimethylbenzylammonium chlorides such as stearyldimethylbenzylammonium chloride and the like; alkylamine salts such as coca-amine acetate, stearylamine acetate and the like; and so on.

Examples of the anionic surfactant include salts of alkylsulfates such as sodium laurylsulfate, triethanolamine laurylsulfate, sodium a higher-alcohol sulfate and the like; salts of poly(oxyethylene)alkylethersulfates such as sodium poly(oxyethylene)laurylether-sulfate, sodium poly(oxyethylene)alkylether sulfate, triethanolamine poly(oxyethylene)-alkylether sulfate and the like; salts of dodecylbenzenesulfonates such as sodium dodecyl-benzenesulfonate and the like; salts of fatty acids such as sodium stearate soap, potassium oleate soap and the like; salts of N-acyl-L-glutamates such as triethanolamine N-acyl-L-glutamate, sodium N-acyl-L-glutamate and the like; poly(oxyethylene)alkylether phosphate; poly(oxyethylene)alkylphenylether phosphate; sodium salt of lauroly sarcosine; sodium alkanesulfonate; sodium alkyldiphenylether disulfonate; sodium dialkyl-sulfosuccinate; sodium alkylnaphthalenesulfonate; and so on.

In some cases, the type of surfactant that can be used may be restricted depending on the use of the object that is obtained after performing the present invention. For example, in the case where the object that is obtained after performing the present invention is used as a raw material of feed or diet, or is food such as salt, edible oil or the like, a surfactant that is permitted to use in foods is used.

The mixing of the object to be treated with the oil may be performed until substantially no water remains in a treated object. In this case, a solid substance and oil remain after performing the method of the present invention. Thus, the solid substance is taken out, and at need, a treatment by which attached oil is removed is performed. For example, the oil is dissolved with hexane or the like. In the case where the oil is used, it is only necessary to remove the solid substance. Especially in the case where the object to be treated is an aqueous solution, the mixing of the object to be treated with the oil may be discontinued after the aqueous solution is concentrated to an intended level. In this case, the object that was obtained by performing of the method of the present invention is left to stand to separate into two layers of an upper layer and a lower layer, which are an oil phase and an aqueous phase, and then necessary phase (the oil phase or the aqueous phase) is taken out so that a solid substance or other phase does not contaminate the necessary phase. Further, depending on the use, entire of the object (which may be one containing substantially no water or may be one in which a certain level of water remains) that was obtained by performing of the method of the present invention may be directly utilized.

In the case where the oil that is obtained after performing the method of the present invention is used, the mixing of the object to be treated with the oil may be performed in the presence of microorganism that shows an effect of preventing oxidation of oil.

Examples of microorganism that shows an effect of preventing oxidation of oil include Koji-kin (fungi belong to Aspergillus). The academic names for various Koji-kin are Aspergillus niger, Aspergillus oryzae, Monascus, and so on. Examples of Koji-kin that belong to Aspergillus niger include Aspergillus awamori, Aspergillus usami, and Aspergillus kawachii. Examples of Koji-kin that belong to Aspergillus oryzae include Aspergillus soya, Aspergillus sojae, and Aspergillus tamari. Examples of Koji-kin that belong to Monascus include Monascus purpureus.

For the addition of Koji-kin, for example, seed rice malt (Tanekoji) is used. The seed rice malt is one obtained by incubating Koji-kin for about 5 days by using rice or the like as a raw material to sufficiently grow spores in a state that the spores adhere to the raw material, and drying the spores and the raw material. One in which the spores adhere to the raw material (for example, one obtained by drying rice to which large amount of spores of Koji-kin adhere) is called as "granular seed rice malt" and another one obtained by gathering spores only by using, e.g., a filter is called as "powdery seed rice malt." The seed rice malt is added to the object to be treated.

Instead of the use of the seed rice malt, solid or liquid fermented Koji (one obtained by incubating microorganism that is useful for fermentation of food in cereal) may also be added, which Koji is preferably one elapsed 6 hours or more from the start of the incubation.

When the Koji-kin is used, the temperature during the mixing of the object to be treated with the oil is generally about 20 to 45 degrees Celsius, and preferably 30 to 40 degrees Celsius. If the temperature excessively increases by, for example, heat during fermentation, cooling is properly performed.

Another examples of microorganism that shows an effect of preventing oxidation of oil include Phizopus and Mucor. They are fungi that exist everywhere.

Some of Phizopus have been used in food industries, for example, one used as in brewage of Shoko-shu (Chinese rice wine) and another one used in the production of Tempe.

Since the Phizopus and *Mucor* also form spores, those that are in a spore state may be added to the object to be treated. In the case where these fungi are used, the temperature during mixing of the object to be treated with the oil is generally about 20 to 45 degrees Celsius, and preferably 30 to 40 degrees Celsius.

The mixing of the object to be treated with the oil may be performed in the presence of an antioxidative substance. This is because an effect that oxidation of oil can be prevented is obtained, in the case where the oil that is obtained by performing the method of the present invention is used.

The antioxidative substances are classified into water-soluble ones and oil-soluble ones. Both of them can be used. Examples of the antioxidative substances include ascorbic acid, glutathione, lipoic acid, uric acid, ethoxyquin, alpha-tocopherol, retinol, ubiquinol, polyphenols, carotenoids, propyl gallate, t-butyl hydroquinone, butylated hydroxyanisole, butylated hydroxytoluene, and so on. These substances are used in amounts that are respectively defined for the substances as proper doses.

The method of the present invention can also be perform by using a cooling tower. The cooling tower to be used may be a commercially available one. One example, in which a cooling tower is used, will be explained based on FIG. 1. FIG. 1 is a schematic and diagrammatic view of vertical section of an example of a cooling tower. However, in FIG. 1 only portions that are necessary for explanation are drawn. An actual cooling tower comprises constitutive elements that are not drawn in FIG. 1, but that are necessary. In the cooling tower 100, there are set a fan 30 at an upper part of it, a loading material 10 around the outer periphery of it, and a storage tank 50 at a lower part of it. There is a pipe 20 between the lower part of the storage tank 50 and the upper part of the loading material 10. There is a pump P in the midstream of the pipe 20, and there are many spray nozzles at the ends of the pipe 20, although the nozzles are not drawn in FIG. 1.

The method of the present invention is performed as follows: the object to be treated and the oil are supplied into the storage tank 50 that is set at a lower part of the cooling tower 100. a mixture of the object to be treated and the oil supplied is transported from the storage tank 50 to an upper part of the cooling tower 100 (more specifically, to an upper part of the loading material 10) through the pipe 20 by a suction power of the pump P and is sprayed from the nozzles that exist at the distal ends of the pipe 20 into the loading material 10. By this spraying, the mixture of the object to be treated and the oil falls into the storage tank 50 through the loading material 10. During passing the mixture of the object to be treated and the oil through the loading material 10, water content of the object to be treated is reduced and an oil-soluble substance in the object to be treated transfers to the oil. The pipe may be set inside a cooling tower.

When the cooling tower 100 is operated, a fan 30 may be revolved and a gas may be passed in a direction that is shown by arrows to which the term "gas" is attached in FIG. 1. By these operations the reduction of water content of the object to be treated is accelerated. In the example that is shown in FIG. 1, the gas horizontally traverses the loading material 10, and the mixture of the object to be treated and the oil falls from the upper part to the lower part of the loading material 10. Thus, this is a direct current type. However, it may be a countercurrent type (i.e., the passing direction of the mixture of the object to be treated and the oil is parallel to the passing direction of the gas).

By using the cooling tower 100, the object to be treated and the oil in the storage tank 50 repeatedly pass the pipe 20 and the loading material 10, and during this time of period, water content of the object to be treated is progressively reduced. In the use of the cooling tower, it is preferable that its operation (the practice of the method of the present invention) is terminated in a state that there remains a certain amount of water in the treated object.

Another method in which the cooling tower is used is as follows: a mixture of the object to be treated and the oil that has been supplied into the storage tank is transported from the storage tank to an upper part of the cooling tower through the pipe by suction power of the pump. then, the mixture is sprayed from nozzles at the upper part of the cooling tower to fall the mixture into the storage tank. Namely, it is a method in which no loading material is used. It may be possible that part of the mixture that has been transported to the upper part of the cooling tower is sprayed into the loading material and the residue is sprayed for the lower part of the cooling tower.

Figure 2:
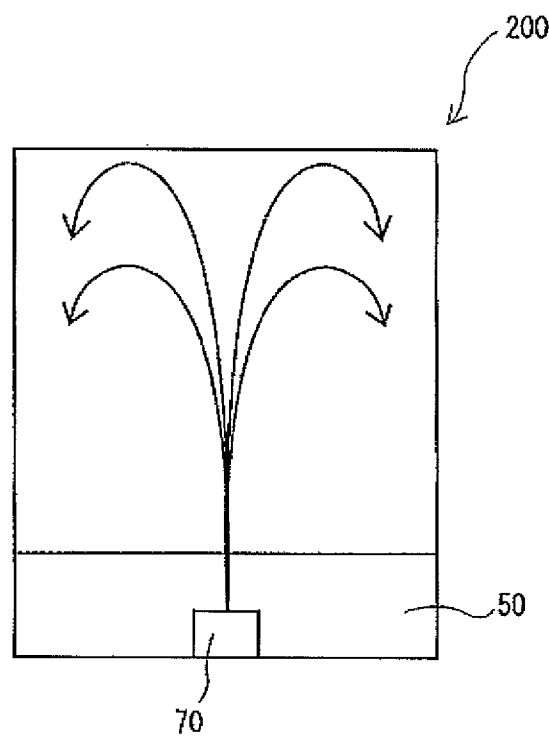
FIG. 2 is a schematic and diagrammatic view showing a constitution that the method of the present invention is performed in a container having a storage tank by using a submersible pump.

The method of the present invention may also be performed by using a submersible pump in a container having a storage tank. Based on FIG. 2, a case where the submersible pump is used will be explained. FIG. 2 is a schematic and diagrammatic view showing a constitution that the method of the present invention is performed in a container having a storage tank by using a submersible pump. Also in FIG. 2, only portions that are necessary for explanation are drawn. An actual apparatus comprises constitutive elements that are not drawn in FIG. 2, but that are necessary. The container 200 has a storage tank 50 at a lower part of it. In the storage tank 50, a submersible pump 70 is set. To the submersible pump 70, a spraying nozzle is connected, although the nozzle is not drawn.

The method of the present invention is performed as follows: the object to be treated and the oil are pooled in the storage tank 50 that is set at a lower part of the container 200. a mixture of the object to be treated and the oil in the storage tank 50 is sucked by the submersible pump 70 and then is squirted from the spraying nozzle that is connected to the submersible pump 70. namely, the mixture is sprayed to be a fountain state. thus, the mixture of the object to be treated and the oil moves upward and thereafter falls into the storage tank 50. during the mixture of the object to be treated and the oil moves upward and falls, water content of the object to be treated is reduced and an oil-soluble substance in the object to be treated transfers to the oil.

In FIG. 2, an example is drawn, in which a closed container is used. However, the container may be an open one. This is because the mixture of the object to be treated and the oil that has been squirted falls with the force of gravity, even if the container has no ceiling. Further, a pathway through which a gas passes may be set in the container.

Next, the method of the present invention will be explained in more detail, depending on each of the uses of treated objects that are obtained by the method of the present invention.

(A) Production of Fuel that is Derived from Organic Waste and Oil

The fuel is produced through a step (1) for reducing water content of an object to be treated by mixing the object to be treated with oil at a temperature that is lower than the boiling point of water, at which temperature the oil is liquid (preferably at 80 degrees Celsius or lower under ordinary pressure), and a step (2) for molding a mixture of the treated object, of which water content has been reduced, and the oil. The water content at the end of the step (1) may be within a rage, in which range it is no problem as fuel. In the case where the water content at the end of the step (1) is substantially 0% by weight, a mixture of oil and a solid substance in a state of powder or the like can be obtained. The molding is performed by using, e.g., an extruder. An adequate additive may be added for molding. As fuel, it is also possible to use the mixture as is of the oil and the treated object, of which water content has been reduced, which mixture is obtained by performing the step (1), without molding.

(B) Production of Feed or Diet, or Fertilizer that is Derived from Organic Waste The feed or diet, or fertilizer is produced through a step (a step (1)) for reducing water content of an object to be treated by mixing the object to be treated with oil at a temperature that is lower than a boiling point of water, at which temperature the oil is liquid (preferably at 80 degrees Celsius or lower under ordinary pressure). After the step (1), a step (step (2)) for separating the treated object, of which water content has been reduced, from the oil may be performed.

The water content after the end of the step (1) is not particularly limited. The water content is an intended level depending on the use of the treated object after the end of the step (1) or a subsequent processing method. The step (1) may be performed until the water content of the treated object becomes substantially 0% by weight. For example, the step (1) is performed until the object to be treated turns to be solid (the concept of the "solid" includes agglomerate and powder; in this case the water content is generally low.), in the step (2) the treated object after the step (1) is separated from the oil, and then additional steps, namely, a step (step (3)) for washing the treated object with a solvent that can dissolve and clean up the oil, and another step (step (4)) for removing the solvent that was used for washing, may be performed. In the case where feed or diet is to be produced and the step for dissolving and cleaning up the oil is performed, the solvent for the use in this purpose is selected among those that are no problem even if any animal takes it in. Examples of such solvent include ethanol, hexane, ether, and so on.

The oil that has used for treatment may be or may not be removed from the treated object, of which water content has been reduced, depending on the object that is to be produced. For example, after the end of the step (1), feed, diet, or fertilizer may be produced by using entire of the treated object, of which water content has been reduced, and entire of the oil that has been used for treatment. Alternatively, although the step (2) is performed, namely, the treated object after the step (1) is separated from the oil by taking out the treated object from the oil, part or all of the oil that contaminates the treated object separated may be removed, or the oil may not be removed at all. Examples of the method for removing part of the oil that contaminates the treated object separated include a method of pressure by using a squeezer such as a screw press or the like, and a filtering method by using a filter aid such as bran and the like.

As organic wastes that can be used as a raw material for feed, diet, or fertilizer, kitchen garbage, a residue by food manufacturing, an effluent of Shochu production, a residue after Sake pressing, an effluent of wine production, an effluent of beer production, an effluent of whisky production, and the like are cited.

Regardless of the level of the water content of the treated object after the step (1), the treated object after the step (1) may be separated from the oil in the step (2) and then the treated object obtained may be subjected to a fermentation step. In the case where the method of the present invention is performed in the presence of microorganism that shows an effect of preventing oxidation of oil, the fermentation may also be one by the microorganism that has been used for performing the method of the present invention. Alternatively, the fermentation may also be one by microorganism that can contribute the fermentation and is newly added after the step (2). The step (2) may also be performed, for example, by performing centrifugation, taking out the treated object from the oil or removing the oil, and compressing the treated object to reduce the content of oil that contaminates the treated object.

The dry feed, diet or fertilize; which has been produced by the above method, may be used alone or after the addition of a vitamin, an antibiotic agent or the like. Moreover, it may be processed to be powder, granule, a compact having a specified form, or the like.

(C) Production of Raw Material for Producing Fertilizer that is Derived from Organic or Inorganic Waste, or Disposal of it as Solid Waste The raw material for producing fertilizer or the like is produced through a step (1) for reducing water content of an object to be treated by mixing the object to be treated with oil at a temperature that is lower than the boiling point of water, at which temperature the oil is liquid (preferably at 80 degrees Celsius or lower under an ordinary pressure), and a step (2) for separating from the oil the treated object, of which water content has been reduced. In the case where the object is a raw material for producing fertilizer, the step (1) is preferably performed until the water content of the treated object at the end of the step (1) comes to be 50% by weight or lower. While, in the case where the treated object is disposed as solid waste, the step (1) is preferably performed until the water content of the treated object at the end of the step (1) comes to be substantially 0% by weight. In the step (2), the treated object after the step (1) is separated from the oil, and then (3) the treated object is washed by using a solvent that can dissolve and clean up the oil, and (4) the solvent that was used for washing is removed.

Regardless of the level of the water content of the treated object after the step (1), the treated object after the step (1) may be separated from the oil in the step (2) and then the treated object obtained may be subjected to a fermentation step. In the case where the method of the present invention is performed in the presence of microorganism that shows an antioxidative property, the fermentation may also be one by the microorganism that has been used for performing the method of the present invention. Alternatively, the fermentation may also be one by microorganism that can contribute the fermentation and is newly added after the step (2). The step (2) may also be performed, for example, by performing centrifugation, taking out the treated object from the oil or removing the oil, and compressing the treated object to reduce the content of oil that contaminates the treated object.

(D) Production of raw material for producing fertilizer that is derived from livestock excreta, fishbone, animal bone, or the like, or disposal of it as solid waste.

For the treatment of livestock excreta, fishbone, animal bone, or the like, the method of the present invention is preferably performed in the presence of rice malt as microorganism that shows an effect of preventing oxidation of oil. Namely, it is produced through a step (1) for reducing water content of an object to be treated by mixing, in the presence of the rice malt, the object to be treated with oil at a temperature that is equal to or lower than the upper temperature limit of the rice malt, and a step (2) for separating from the oil the treated object, of which water content has been reduced. Preferably, the step (1) is performed until the water content of the treated object at the end of the step (1) comes to be substantially 0% by weight. In the step (2), the treated object after the step (1) is separated from the oil, and then (3) the treated object is washed by using a solvent that can dissolve and clean up the oil, and (4) the solvent that was used for washing is removed. By this method, offensive odor derived from livestock excreta, fishbone, animal bone, or the like comes to be next to zero.

(E) Method for Producing Salt and Method for Obtaining Fresh Water from Sea Water Salt is produced through a step (1) for evaporating water to precipitate salt by mixing sea water or a concentrate of it with oil at a temperature that is lower than the boiling point of water, at which temperature the oil is liquid (preferably at 80 degrees Celsius or lower under ordinary pressure), and a step (2) for separating from the oil the precipitated salt. In the step (2), part of the precipitated salt may not be used, to which salt the oil contacts.

When the step (1) is performed, by flowing a gas on or above the mixture of the sea water or the concentrate of it and the oil, and leading the gas that has passed on or above the mixture of the sea water or the concentrate of it and the oil to, e.g., a condenser, water vapor that has been held by the gas is collected as fresh water. In this case, the gas that has been flown on or above the mixture of the sea water or the concentrate of it and the oil can be used in circles.

By applying the above method, a concentrate of sea water can be produced by using sea water as a raw material, producing a concentrate of the sea water by performing the step (1) so as not to precipitate salt, and subjecting the concentrate to the step (2) to separate the concentrate from the oil.

(F) Extraction of Oil-Soluble Substance from Hydrous Tea-Leaf,

In tea-leaf, useful oil-soluble substances are also contained. The method of the present invention can be applied, for example, to extract into oil useful oil-soluble substances from hydrous tea-leaf after production of green-tea beverage. Namely, (1) an oil-soluble substance in tea-leaf is extracted into oil by mixing hydrous tea-leaf with oil at a temperature that is lower than the boiling point of water, at which temperature the oil is liquid (preferably at 80 degrees Celsius or lower, more preferably at 40 degrees Celsius or lower, under ordinary pressure), and then (2) the oil is separated from the tea-leaf. The oil that can be obtained by performing this method, into which the oil-soluble substance in the tea-leaf has been dissolved, is beautiful, has a green color, and can be used as, e.g., food. In the case where the oil is used as food, edible oil is used also for performing the method of the present invention.

The tea-leaf comprises an antioxidative substance. However, in the case where it is desired to further prevent oxidation of oil in performing the method of the present invention, it is preferable that the method of the present invention is performed at a lower temperature, and/or, that the method of the present invention is performed in the presence of microoragasism that shows an effect of preventing oxidation of oil, such as Koji-kin or the like, at a temperature equal to or lower than the upper temperature limit of the microorganism.

(G) Extraction of Oil-Soluble Substance from Grinded Nut of Palm or Grinded Nut of Camellia The nut of palm and the nut of camellia are useful sources of oil. These nuts comprise an aqueous liquid in addition to oil. Thus, to gather oil from these nuts, the method of the present invention can be applied. Below, a method for gathering oil from palm nuts will be described. However, the case of camellia nut is the same.

By (1) mixing grinded nuts of palm (a mixture of a solid substance such as shell, oil, and aqueous liquid) with palm oil at a temperature that is lower than the boiling point of water, at which temperature the palm oil is liquid (preferably at 80 degrees Celsius or lower, more preferably at 30 to 40 degrees Celsius, under ordinary pressure), palm oil in grinded nuts of palm is extracted into the palm oil that has been used for mixing and then (2) after the palm oil has been extracted, the oil is separated from a mixture of the solid substance such as shell or the like and the aqueous liquid, or from the solid substance such as shell or the like (in the case where the step (1) has been performed until the water content comes to be substantially 0% by weight).

By performing this method, only palm oil can be certainly extracted from the grinded nuts of palm. Further, if the step (1) is performed until the water content comes to be substantially 0% by weight, only a solid substance such as shell or the like remains. Therefore, the problem of the treatment of the palm oil effluent after obtaining palm oil by compression can be solved. Further, the palm oil can be gathered in a higher efficiency than that in the conventional one for obtaining the palm oil.

The oil to be used is preferably the same as that to be gathered. However, the oil to be obtained may be an oil mixture, or it is desired to obtain an oil mixture, any oil may be used, the kind of which differs from the oil to be gathered.

To prevent or reduce the oxidation of palm oil in the practice of this method, it is preferable that the method of the present invention is performed at a lower temperature, is performed in the presence of microorganism that shows an effect of preventing oxidation of oil, such as Koji-kin or the like, at a temperature equal to or lower than an upper temperature limit of the microorganism, or is performed in the presence of an antioxidative substance. Among these measures, it is particularly preferable to perform the method of the present invention in the presence of microorganism that shows an effect of preventing oxidation of oil, such as Koji-kin or the like, at a temperature equal to or lower than an upper temperature limit of the microorganism. An effect that the melting point of the palm oil drops can also be obtained by the use of the Koji-kin or the like.

(H) Production of Compost (Part 1)

The compost is produced through a step (1) for reducing water content of an object to be treated by mixing the object to be treated such as kitchen garbage, a residue by food manufacturing, or the like, with oil at a temperature that is lower than the boiling point of water, at which temperature the oil is liquid (preferably at 80 degrees Celsius or lower under ordinary pressure), and a step (2) for fermenting the mixture of the oil and the treated object, of which water content has been reduced, with microorganism. The water content at the end of the step (1) may be within a rage, in which range it is no problem to do fermentation for producing compost. Also, the oil may be within a rage, in which range it is no problem to do microorganism fermentation for producing compost. Further, the microorganism to be used may also be one that is usually used in the production of compost.

(I) Production of Compost (Part 2)

The compost is produced through a step (1) for reducing water content of an object to be treated by mixing the object to be treated such as kitchen garbage, a residue by food manufacturing, or the like, with oil at a temperature that is lower than the boiling point of water, at which temperature the oil is liquid (preferably at 80 degrees Celsius or lower under ordinary pressure), a step (2) for separating from the oil the treated object, of which water content has been reduced, and a step (3) for fermenting the treated object that has been obtained in the step (2), of which water content has been reduced, with microorganism. The water content at the end of the step (1) may be within a rage, in which range it is no problem to do fermentation for producing compost. The step (2) can be performed by, for example, performing centrifugation, taking out the treated object from the oil, and compressing the treated object to reduce the content of oil that contaminates the treated object. The amount of the oil that remains in the treated object may be within a rage, in which range it is no problem to do microorganism fermentation for producing compost. Also, the microorganism to be used may be one that is usually used in the production of compost.

(J) Production of Liquid Feedstuff

The liquid feedstuff is produced through a step (1) for reducing water content of an object to be treated (to be preferably 75 to 95% by weight, more preferably 90 to 96% by weight) by mixing the object to be treated such as kitchen garbage, a residue by food manufacturing, or the like, with oil at a temperature that is lower than the boiling point of water, at which temperature the oil is liquid (preferably at 80 degrees Celsius or lower under ordinary pressure), and a step (2) for separating from the oil the treated object, of which water content has been reduced. In the step (2), it is not necessarily required to perfectly separate into an aqueous phase and an oil phase. In so far as the aqueous phase can be allowed as a liquid feedstuff, the aqueous phase may be contaminated with a certain amount of oil. Further, as a part of the step (2), centrifugation or compression may be performed.

In the case where the object to be treated is, e.g., a vegetable, its water content is about 98% by weight, its nutritive value is also low, it does not become a liquid because there is high in fiber, and it is difficult to recycle it. However, if such a vegetable is subjected to the method of the present invention, a liquid feedstuff having appropriate water content can be readily obtained.

In the production of the liquid feedstuff, it is preferable to perform the method of the present invention in the presence of microorgasnism that shows an effect of preventing oxidation of oil, preferably Koji-kin. Because such microorganism also shows a function of decomposing fiber, liquid feedstuff can be exactly obtained. Further, if the Koji-kin is used, the aqueous phase (liquid feedstuff) after separating from the oil has a relatively low pH (for example, its pH is about 4). Thus, a feature that it difficultly decomposes is also shown. Moreover, after performing the method of the present invention, namely, after the step (2), a fermentation step may be set. In this case, the fermentation may be one by using the microorganism that has been used for performing the method of the present invention, or may be another one by using microorganism that can contribute the fermentation and is newly added after the step (2).

(K) Production of fishmeal

The fishmeal is produced through a step (1) for reducing water content of a dead fish or garbage of a fish by mixing the dead fish or garbage of the fish with oil containing microorganism that shows an effect of reventing oxidation of oil, preferably Koji-kin, at a temperature that is lower than the boiling point of water, at which temperature the oil is liquid, and at need also through a step (2) for separating from the oil the treated object, of which water content has been reduced.

By performing the step (1), the dead fish or garbage of the fish can be dried without generating offensive odor. If the drying is sufficiently performed, a powdery solid substance is resulted. By performing the step (2) after the step (1), and further removing the oil that contaminates the separated powdery solid substance by using an oil-soluble solvent, powder having a high fluidity (fishmeal) can be obtained-Depending on its use, fishmeal containing part or all of the oil that has been used in the step (1) may be produced. Also, "for separating from the oil the treated object, of which water content has been reduced" in the step (2), the treated object may be taken out from the oil. After performing the step (2), it is not necessary to completely remove the oil that contaminates the treated object, of which water content has been reduced. The fishmeal produced in such a state that all or part of the oil that has been used for the treatment remains in the treated object is also one that was produced by the method of the present invention. By performing the method of the present invention, it is also possible to realize the water content of fishmeal of substantially 0% by weight.

Also in the production of fishmeal, the method that was described in the production of compost (part 2) can be applied. The step (3) is a fermentation step, and usually microorganism that contributes to fermentation is added. However, in the case where the method of the present invention (a method for producing fishmeal) is performed in the presence of microorganism that shows an effect of preventing oxidation of oil, and the microorganism is one that contributes to fermentation (for example, Koji-kin), the step (3) can be performed without newly adding microorganism.

(L) Drying Of Blood Of Livestock

The drying of blood is performed through a step (1) for reducing water content of blood by mixing the blood that originates from a place for slaughter treatment with oil at a temperature that proteins in the blood do not denature (preferably at 40 degrees Celsius or lower), at which temperature the oil is liquid, and a step (2) for separating from the oil the blood, of which water content has been reduced.

The drying of the blood can be performed by almost the same way as that of (J) production of fishmeal, and powder of blood can be obtained. Therefore, also in this case, it is preferable to perform the method of the present invention in the presence of Koji-kin.

Also for the drying of the blood, the method that was described in the production of compost (part 2) can be applied. In the case where the method of the present invention (a method for drying blood) is performed in the presence of Koji-kin, the step (3) can be performed without newly adding microorganism, and the fermentation may be performed by the Koji-kin.

EXAMPLES

Hereinafter, the present invention will be specifically explained in reference to examples, Example 1

Evaporation of Water Under Mixing of Water with Oil (1) Into an Erlenmeyer flask of 500 mL-volume, tap water (100 mL or 200 mL), or tap water (100 mL) and waste oil of cooking oil for Tenpura (100 mL) was (were) poured, and stirring was performed at 30 degrees Celsius at 200 rpm for 24 hours. Table 1 shows amounts of evaporated water.

TABLE 1

| Sample | Water loss by evaporation | Water loss by evaporation/ original amount of water |
|---|---|---|
| 100 mL of water | 14 mL | 14.0% by volume |
| 200 mL of water | 15 mL | 7.5% by volume |
| 100 mL of water + 100 mL of oil | 24 mL | 24.0% by volume |

(2) Into a measuring cylinder of 1 L-volume, tap water (200 mL or 400 mL), or tap water (200 mL) and waste oil of cooking oil for Tenpura (200 mL) was (were) poured, and bubbling was performed at 30 degrees Celsius for 24 hours by blowing air at a rate of 2.5 L/minute. Table 2 shows amounts of evaporated water.

TABLE 2

| Sample | Water loss by evaporation | Water loss by evaporation/ original amount of water |
|---|---|---|
| 200 mL of water | 35 mL | 17.5% by volume |
| 400 mL of water | 40 mL | 10.0% by volume |
| 200 mL of water + 200 mL of oil | 60 mL | 30.0% by volume |

It is clarified from Tables 1 and 2 that water readily evaporates by mixing the oil with the water by means of stirring or bubbling to make a temporary, namely, labile, emulsified state, as compared to the case of water only.

Example 2

Influences of Ratio Between Water and Oil and Absolute Amount Against Evaporation of Water (1) Into an Erlenmeyer flask of 500 mL-volume, tap water and waste oil of cooking oil for Tenpura were poured, and stirring was performed at 30 degrees Celsius at 200 rpm for 24 hours. Table 3 shows amounts of evaporated water.

TABLE 3

| Sample | | | |
|---|---|---|---|
| Oil (g) | Water (g) | Water loss by evaporation (g) | Water loss by evaporation/original amount of water (% by weight) |
| 0 | 200 | 15.2 | 7.6 |
| 50 | 150 | 13.9 | 9.3 |
| 80 | 120 | 17.2 | 14.3 |
| 100 | 100 | 27.9 | 27.9 |
| 120 | 80 | 17.9 | 22.4 |
| 150 | 50 | 12.8 | 25.6 |

It became clear from Table 3 that water was able to be more efficiently evaporated at a ratio of oil/water of 1 or more (weight ratio).

(2) Into a measuring cylinder of 1 L-volume, tap water and waste oil of cooking oil for Tenpura were poured, and bubbling was performed at 30 degrees Celsius for 24 hours by blowing air at a rate of 2.5 L/minute. Table 4 shows amounts of evaporated water.

TABLE 4

| Sample | | | |
|---|---|---|---|
| Oil (g) | Water (g) | Water loss by evaporation (g) | Water loss by evaporation/original amount of water (% by weight) |
| 200 | 200 | 56.9 | 28.5 |
| 300 | 300 | 66.7 | 22.2 |

It is thought that the difference between water-reducing rates (water loss by evaporation/original amount of water) based on the differences of absolute amounts of water and oil depends on the difference of stirring efficiency. This is because the ratios of the water to the oil were the same and the volumes of air blown were the same.

Example 3

Use of Engine Oil

Into a measuring cylinder of 1 L-volume, tap water (200 mL) and engine oil (200 mL) were poured, and bubbling was performed at 30 degrees Celsius for 24 hours by blowing air at a rate of 2.5 L/minute. The amount of water evaporated was determined, and tap water was added in such an amount that it is the same as the loss of water. For an additional 24 hours, the bubbling was performed in the same way. This method was continued for 5 days. Table 5 shows water losses per 1 hour.

TABLE 5

| | Water loss (mL) during 24 hours | Water loss per one hour (mL/hour) |
|---|---|---|
| After 1 day | 42.4 | 1.77 |
| After 2 days | 39.9 | 1.65 |
| After 3 days | 37.6 | 1.46 |
| After 4 days | 33.1 | 1.50 |
| After 5 days | 36.5 | 1.52 |

The water is not incorporated into the oil, but is removed by evaporation. Thus, the evaporation efficiency of water do not change over time.

Example 4

Influence of Surfactant

Into an Erlenmeyer flask of 200 mL-volume, tap water (50 g; with the proviso that it was 50 g including the water that was derived from a surfactant, if the surfactant was not a product of 100%), waste oil of cooking oil for Tenpura (50 g), and a surfactant (an amount that the amount of the active component became 0.1% by weight) were poured, and shaking was performed at 30 degrees Celsius at 200 rpm for 24 hours. The amount of water evaporated was determined. The surfactants used are as follows. Also, as a control, a system in which the surfactant was not added was treated in the same way and the determination was performed. Table 6 shows water losses and rates of water losses (water loss by evaporation/original amount of water).

Anionic surfactant: sodium salt of a fatty acid
Cationic surfactant: benzalkonium chloride (10% solution)
Nonionic surfactant: Poly(oxyethylene)sorbitan monooleate
Amphoteric surfactant: 3-[3-choloroamidepropyl]dimethylammonio]-2-hydroxy-1-propane sulfonate

TABLE 6

| | After 24 hours | |
| --- | --- | --- |
| Type of surfactant | Water loss (g) | Rate of water loss (% by weight) |
| Control | 15.0 | 30.0 |
| Anionic surfactant | 30.1 | 60.2 |
| Cationic surfactant | 36.1 | 72.2 |
| Nonionic surfactant | 15.7 | 31.4 |
| Amphoteric surfactant | 19.3 | 38.6 |

After stopping the shaking, the flask was left to stand for 24 hours. The lower layer (aqueous phase) separated was taken out, and the transmittance was determined at 660 nm by using a spectrophotometer. Table 7 shows the result.

TABLE 7

| Type of surfactant | Transmittance (%) |
| --- | --- |
| Control | 90.2 |
| Anionic surfactant | 21.6 |
| Cationic surfactant | 56.4 |
| Nonionic surfactant | 0.3 |
| Amphoteric surfactant | 4.6 |

In the case where a surfactant having a strong emulsifying power is used, namely, the transmittance of the aqueous phase after separation is low, oil membrane (an outer phase in an emulsified state) is stably formed around spheres of water (inner phases in an emulsified state). In this case, it cannot be said that evaporation of water is accelerated as compared to the case where no surfactant is contained, as is clear from Tables 6 and 7. In the case where an anionic or a cationic surfactant is used, which surfactant forms a labile emulsified state during mixing of the water with the oil, the water comes to be smaller spheres (inner phases in an emulsified state) during stirring as compared to the case (control) where there is no surfactant, and thus the total surface area of the water is sized up. Also, the emulsified state is labile. Therefore, the spheres of water (inner phases in an emulsified state) are repeatedly formed and decomposed, and there is a moment when there is no oil membrane (an outer phase in an emulsified state) around spheres of water. Because of these reasons it is thought that the evaporation of water is accelerated moreover. The reason why the transmittance of the control was not 100% is thought that a surfactant was contained in the waste oil of the cooking oil for Tenpura.

Example 5

Drying of Effluent of Shochu Production

Into an Erlenmeyer flask of 500 mL-volume, 30 g of an effluent of Shoehu production and 150 g of waste oil of cooking oil for Tenpura were poured. After lidding the flask, it was sterilized at 121 degrees Celsius for 15 minutes in an autoclave, Thereafter, it was cooled by leaving it stand at room temperature. The mixture of the effluent of Shochu production with the waste oil was stirred at room temperature at 200 rpm for 95 hours in such a state that the lid had been taken off. By determining the weight of the Erlenmeyer flask that comprises the effluent of Shochu production and the waste oil before the start of the experiment and at midstream of it reduced amounts of the weight (since one that reduced was water in the effluent of Shochu production, the amount will be called as "water loss") and rates of water loss (water loss/original weight of the effluent of Shochu production) were calculated. Table 8 shows the results.

TABLE 8

| Hours | Water loss (g) | Rate of water loss (% by weight) |
| --- | --- | --- |
| 0.0 | 0.0 | 0.0 |
| 14.0 | 10.1 | 33.7 |
| 23.0 | 14.5 | 48.3 |
| 38.0 | 20.7 | 69.0 |
| 48.5 | 24.5 | 81.7 |
| 62.0 | 26.0 | 86.7 |
| 67.5 | 27.3 | 91.0 |
| 71.5 | 27.5 | 91.7 |
| 86.0 | 28.1 | 93.7 |
| 95.0 | 28.4 | 94.6 |

It is said that the water content of the effluent of Shochu production is about 95% by weight. As is clear from Table 8, after 95 hours, the water that had contained in the effluent of Shochu production had been substantially lost. Actually, the waste oil and a solid substance remained in the Erlenmeyer flask. The solid substance was washed with ether after it had been taken out, and then dried in air. As a result, it became one having a high fluidity. At 67.5 hours after a start of the stirring, a small amount (1 ml) of an aqueous phase was sampled and numbers of viable bacteria and Koji-kin in it were respectively counted. Each number was 0 (zero). Therefore, solid contents in the effluent of Shochu production were not decomposed by bacteria or fungi.

Example 6

Drying of Slops

Into a tank of 1 ton-volume, 100 kg of slops was put and 600 L of waste oil of cooking oil for Tenpura was poured. The temperature of a heater was set at 40 degrees Celsius, and they were agitated at 600 rpm, while blowing air with a blower from a lower side to an upper side in the tank. Height of tank content was measured and rate of volume loss was calculated. The temperature of the tank content was also determined. Table 9 shows the results.

TABLE 9

| Hours | Rate of volume loss (%) | Temperature of tank content itself (° C.) |
|---|---|---|
| 0.0 | — | — |
| 15.0 | 50.0 | — |
| 24.0 | 62.5 | 38 |
| 38.5 | 87.5 | 37 |
| 41.5 | 90.6 | 38 |

Also in the case where the objects to be treated were slops, the water certainly evaporated and the volume of them was reduced.

Example 7

Drying of Effluent of Shochu Production

Into an Erlenmeyer flask of 500 mL-volume, an effluent of Shochu production and waste oil of cooking oil for Tenpura were poured. They were stirred at 30 degrees Celsius at 200 rpm. This operation was continued for 7 days. Table 10 shows amounts of water evaporated (water loss) and rates of water loss (water loss/original weight of the effluent of Shochu production).

TABLE 10

| Sample | | Water loss (upper column; g) and Rate of water loss (lower column; % by weight) | | | | | | |
|---|---|---|---|---|---|---|---|---|
| Waste oil (g) | Effluent of Shochu production (g) | After 1 day | After 2 days | After 3 days | After 4 days | After 5 days | After 6 days | After 7 days |
| 0 | 200 | 19.9 | 35.1 | 50.6 | 64.4 | 79.9 | 100.4 | 116.7 |
|  |  | 10.0 | 17.6 | 25.3 | 62.2 | 40.0 | 50.2 | 58.4 |
| 70 | 130 | 15.2 | 30.1 | 45.0 | 59.8 | 91.9 | 106.6 | 118.5 |
|  |  | 11.7 | 23.2 | 34.6 | 46.0 | 70.7 | 82.0 | 91.1 |
| 100 | 100 | 14.3 | 39.1 | 67.7 | 85.0 | 93.4 | 93.9 | 93.8 |
|  |  | 14.3 | 39.1 | 67.7 | 85.0 | 93.4 | 93.9 | 93.8 |
| 130 | 70 | 14.2 | 39.4 | 58.7 | 64.9 | 65.3 | 65.3 | 65.4 |
|  |  | 20.3 | 56.3 | 83.9 | 92.7 | 93.3 | 93.3 | 93.4 |

As is clear from Table 10, with increasing the ratio of the waste oil to the effluent of Shochu production, the water-reducing efficiency increased. In the systems of the waste oil/the effluent of Shochu production (weight ratio) of 70/130, 100/100, and 130/70, there were substantially no water and only the waste oil and a solid substance remained at the end of the experiment, This dovetails with the fact that the water content of the effluent of Shochu production is about 95% by weight.

Example 8

Drying of Effluent of Palm Oil Production (POME)

Into an Erlenmeyer flask of 500 mL-volume, an effluent at the production of palm oil and waste oil of cooking oil for Tenpura were poured, and were stirred at 30 degrees Celsius at 200 rpm. This operation was continued for 1 day. Table 11 shows amounts of water evaporated (water loss) and rates of water loss (water loss/original weight of the palm oil effluent).

TABLE 11

| Samples | | | |
|---|---|---|---|
| Waste oil (g) | POME (g) | Water loss (g) | Rate of water loss (% by weight) |
| 0 | 200 | 27.0 | 13.5 |
| 70 | 130 | 16.7 | 12.8 |
| 100 | 100 | 15.2 | 15.2 |
| 130 | 70 | 15.4 | 22.0 |

Example 9

Study of Influence of Aeration Amount Against Evaporation Efficiency

Into a cylindrical container having a diameter of 112 cm, 250 g of canola oil and 250 g of water were poured. Aeration (bubbling) was performed at 30 degrees Celsius for 24 hours by using an air stone for goldfishes. The number of kinds of aeration amounts was 9 as shown in Table 12. Table 12 shows reduction amounts of water (water loss) and reduction rates (rates of water loss).

TABLE 12

| | Aeration amount (L/minutes) | | | | | | | | |
|---|---|---|---|---|---|---|---|---|---|
| | 0.5 | 1.0 | 2.0 | 3.0 | 3.5 | 4.5 | 6.0 | 8.0 | 10.0 |
| Water loss (g) | 22.7 | 28.3 | 57.2 | 82.3 | 73.6 | 87.6 | 112 | 138 | 143 |
| Rate of water loss (% by weight) | 9.1 | 11.3 | 22.9 | 32.9 | 29.4 | 35.0 | 44.8 | 55.2 | 57.2 |

Example 10

Drying of Active Sludge

Into an Erlenmeyer flask of 500 mL-volume, active sludge derived from sewage was put and waste oil of cooking oil for Tenpura was poured, and were stirred at a humidity of 35% at 30 degrees Celsius at 200 rpm. After 24 hours, the weight was determined and the water loss was calculated. Then, in examination numbers 1-3, the stirring was continued as is in an additional 24 hours under same conditions, the weight was successively determined, and the water loss was calculated. In examination number 4, there was substantially no water (10 g (original amount of active sludge)−0.9 g (amount of reduced water)=0.1 g) in the active sludge after 24 hours. Therefore, after adding 9.5 g of active sludge, the stirring was continued in an additional 24 hours under same conditions, the weight was successively determined, and the water loss was calculated. Table 13 shows the results.

TABLE 13

| Examination number | Waste oil (g) | Active sludge (g) | Water loss after 24 hours (g) | Water loss (g) after restart (upper column: water loss per 1 hour; lower column: total water loss after restart) | | | | | |
|---|---|---|---|---|---|---|---|---|---|
| | | | | 1 hour | 2 hours | 3 hours | 4 hours | 5 hours | 24 hours |
| 1 | 0 | 100 | 32.5 | 0.4 | 0.1 | 0.7 | 0.4 | 1.4 | — |
| | | | | 0.4 | 0.5 | 1.2 | 1.6 | 3.0 | 5.4 |
| 2 | 50 | 50 | 12.0 | 1.5 | 0.1 | 1.2 | 0.4 | 0.5 | — |
| | | | | 1.5 | 1.6 | 2.8 | 3.2 | 3.7 | 5.9 |
| 3 | 70 | 30 | 11.6 | 0.7 | 0.5 | 0.3 | 0.8 | 0.8 | — |
| | | | | 0.7 | 1.2 | 1.5 | 2.3 | 3.1 | 5.4 |
| 4 | 90 | 10 | 9.9 | 0.9 | 0.4 | 1.2 | 0.6 | 0.6 | — |
| | | | | 0.9 | 1.3 | 2.5 | 3.1 | 3.7 | 6.0 |

Example 11

Drying of Sea Water

Into a measuring cylinder of 1 L-volume, 200 g of sea water and 200 g of canola oil were poured. Bubbling was performed by blowing air at a rate of 2.5 L/minute, while stirring them at 30 degrees Celsius at 950 rpm. This was continued for 7 days. At every 24 hours, the amount of water evaporated (water loss) was determined and calculated, and the condition was concurrently observed. Table 14 shows the results.

TABLE 14

| | After 1 day | After 2 days | After 3 days | After 4 days | After 5 days | After 6 days | After 7 days |
|---|---|---|---|---|---|---|---|
| Water loss (g) | 40.7 | 85.3 | 126.2 | 159.3 | 183.9 | 192.4 | 193.2 |
| Rate of water loss (% by weight) | 20.4 | 42.7 | 63.1 | 79.7 | 92.0 | 96.2 | 96.6 |
| Note | | | There was crystalline salt | The surface of liquid bubbled | | | |

After the experiment was completed, a solid substance (comprising salt) was gathered, washed with hexane, and dried at 80 degrees Celsius for 1 hour. The weight of the solid substance was 6.66 g (original weight of sea water−amount of water evaporated=6.8 g; the weight nearly corresponds to this numerical value). While, the weight of the canola oil was 199.4 g, and this was almost the same as the original weight.

Example 12

Using of Cooling Tower

A compact cooling tower was prepared, which has a cooling calorie of 13.6 kw, circulatory amount of water of 39 L/minutes, bore of a blower of 300 mm, wattage used in an electric motor of 50 W, and pipe bore of 25 A. Into a storage tank of this cooling tower, 10 kg of an effluent of Shochu production (water content: 95% by weight) and 80 kg of waste oil of cooking oil for Tenpura were poured. A mixture of the effluent of Shochu production with the waste oil of cooking oil for Tenpura was lifted to an upper part of the cooling tower by operating a pump, was dropped from above a loading material, and was recovered in the storage tank. These operations were continuously practiced.

The pump was stopped after 24 hours, the reduced amount (amount of water evaporated) was determined, then 10 kg of an effluent of Shochu production was added, and the pump was again operated. These operations were performed for 7 days. Table 15 shows the results.

TABLE 15

| | Additive amount of waste oil of cooking oil for tempura (kg) | Additive amount of effluent of Shochu production (kg) | Reduced amount (g) |
|---|---|---|---|
| 0 day (at start) | 80 | 10 | — |
| 1 day | | 10 | 7 |
| 2 days | | 10 | 4 |
| 3 days | | 10 | 12 |
| 4 days | | 10 | 8 |

TABLE 15-continued

| | Additive amount of waste oil of cooking oil for tempura (kg) | Additive amount of effluent of Shochu production (kg) | Reduced amount (g) |
|---|---|---|---|
| 5 days | | 10 | 13 |
| 6 days | | 10 | 6 |
| 7 days | | — | 18 |

As shown in Table 15, 70 kg in total of the effluent of Shochu production was added and its reduced amount was 68 kg in total. Thus, the reduction rate was 97% by weight of the effluent of Shochu production added. This is a value that corresponds to almost the water content of the effluent of Shochu production. Only the effluent of Shochu production was poured into the cooling tower and the same experiment was tried. However, the effluent of Shochu production was not able to be sucked with the pump and the operation of the pump was quickly disengaged.

Example 13

Study of Influence of Treatment Temperature to Properties of Treated Object

Into a container, 2 litters of an effluent of Shochu production (water content: 95% by weight) and 18 litters of waste oil of cooking oil for Tenpura were poured. By blowing air at a rate of 4 litters/minute while heat-retaining the container at 70 degrees Celsius, the effluent of Shochu production was suspended in the waste oil of cooking oil for Tenpura. At 24 hours after the start of the blowing of air, all of the water that had contained in the effluent of Shochu production was evaporated, and only the waste oil of cooking oil for Tenpura and a solid derived from the effluent of Shochu production remained. The solid was taken out, the attached oil was removed with n-hexane, and the weight and the water content of the solid were determined. Next, this solid was left to stand at room temperature for 24 hours, and thereafter its weight and water content were determined.

Exactly the same method as that described above was performed, except that the heat-retaining temperature was 80 degrees Celsius, 85 degrees Celsius, or 90 degrees Celsius, Table 16 shows the results.

TABLE 16

| Treatment temperature | 70° C. | 80° C. | 85° C. | 90° C. |
|---|---|---|---|---|
| Weight of obtained solid | 110 g | 112 g | 110 g | 114 g |
| Water content of obtained solid | 0% by weight | 0% by weight | 0% by weight | 0% by weight |
| Weight of solid after it has been left to stand at room temperatures for 24 hours | 110 g | 112 g | 121 g | 128 g |
| Water content of solid after it has been left to stand at room temperatures for 24 hours | 0% by weight | 0% by weight | 10% by weight | 11% by weight |

As is clear from Table 16, it became clear that although dry solid can be obtained once by performing the method of the present invention at a temperature of 85 degrees Celsius or above, the solid absorbs moisture thereafter. Therefore, it is preferable to perform the method of the present invention at a temperature of 80 degrees Celsius or lower.

Example 14

Extraction of Camellia Oil

Into a flask of 350 mL-volume, 36 g of roughly crushed camellia nuts (content of an oil and fat: 35% by weight) were put and 15 g of water was poured, and they were left to stand for about 6 hours. This operation was performed to restore the camellia nuts to the same condition as that of fresh ones that had not been dried, because the camellia nuts obtained had dried (water content: 6% by weight).

Then, 100 g of rapeseed oil was poured into the flask. The flask was shaken at 30 degrees Celsius for 12 hours. After the completion of the shaking, centrifugation (4000 rpm, 15 minutes) was performed. After the centrifugation, the upper layer (an oil and fat fraction) was 111 g and the lower layer (water and a solid content) was 22 g.

From the above description, it was understood that the evaporated water amount was 17 g (=(35+15+100)−(111+22)), and the oil that had been extracted from the camellia nuts was 11 g (=111−100). Also, the oil-extraction rate from the camellia nuts was 89.8% by weight (=11/(35×0.35)×100). Since the extraction rate of the camellia oil by the compressing method is about 50% by weight, the method of the present invention is extremely high in extraction efficiency.

In the lower layer after the centrifugation, proteins, carbohydrates, a small amount of oils and fats, and water are contained. However, the quantity of the water contained is small, Thus, it can be stored as it is. Also the lower layer can be used as feed or fertilizer.

Furthermore, the method of the present invention does not require dry and compression treatments of nuts. Thus, there is also an advantage that the effort and production cost can be drastically reduced.

Example 15

Drying of Garbage of Fish

Into an Erlenmeyer flask of 3 L-volume, 100 g of garbage of fishes was put, and 50 g of water and 900 g of waste oil of cooking oil for Tenpura were poured. The flask was shaken at 30 degrees Celsius for 12 hours. After the completion of the shaking, the obtained mixture was centrifuged (4000 rpm, 15 minutes) and the oil separated was removed.

The amount of the oil after centrifugation (the waste oil of cooking oil for Tenpura and oil-soluble substances derived from the garbage of fishes) was 830 g, and others were 116 g. Therefore, by performing this method, 104 g of water (mainly) was evaporated and removed. Also, the components (solid contents) other than oil after the centrifugation mainly consisted of proteins, and water was substantially 0% by weight. Therefore, it is thought that this solid component can be used as a high-quality raw material for feed. Further, it is thought that this solid component can be stored as it is, because the possibility of development of fungi in this solid content or that of decay of the solid content is extremely low,

Example 16

Drying of Poultry Manure

Into an Erlenmeyer flask of 3 L-volume, 50 g of poultry manure was put, and 450 g of waste oil of cooking oil for Tenpura was poured. The flask was shaken at 30 degrees Celsius for 24 hours. After the completion of the shaking, the obtained mixture was centrifuged (4000 rpm, 15 minutes) and the oil separated was removed.

The amount of the oil after the centrifugation (the waste oil of cooking oil for Tenpura and oil-soluble substances derived from the poultry manure) was 420 g, and others were 15 g. Therefore, by performing this method, 65 g of water (mainly) was evaporated and removed. Also, components (solid contents) other than oil after the centrifugation mainly consisted of fibers that had not been digested and proteins, and water was about 3% by weight. Therefore, it is thought that these solid contents can be used as raw materials for feed.

Example 17

Growth Promoting Effect of Feed of the Present Invention (Part 1)

The dry substance (one that was taken out from the waste oil of cooking oil for Tenpura that had been used for treatment, to which part of the waste oil adhered) that had been obtained by performing Example 15 was subjected to componential analyses. As a result, crude protein was 38.1% by weight and crude fat is 26.9% by weight. Namely, it was clarified that the dry substance that had been obtained by performing Example 15 was a high-protein and high calorie feed. This dry substance was fed to yellow tail as a part of feed, and the presence or absence of a growth promoting effect was examined.

1. Experimental Conditions

Objective fish: farmed yellow tail

Number of fishes at the start of the examination: 2,000 for each experimental group Feed for the examination group: a mixture of a commercially available pelleted feed for aquaculture (96% by weight) with the feed that had been obtained in Example 15 (4% by weight)

Feed for the control group: Only the commercially available pelleted feed for aquaculture Examination period: 3 months for average body length, 5 months for average weight, and 7 months for number of surviving fishes 2. Results Table 17 shows the results. As is clear from Table 17, the average body length, the average weight, and the number of surviving fishes of the examination group were significantly larger than those of the control group, respectively. Namely, it was confirmed that the feed that had been prepared according to the method of the present invention had an effect of increasing immunity and a growth promoting effect.

TABLE 17

| | Average body length (cm) | | | Average weight (kg) | | | Number of surviving fishes (fishes) | |
|---|---|---|---|---|---|---|---|---|
| | Before start of Examination | After 3 months | Increasing rate | Before start of Examination | After 5 months | Increasing rate | After 7 months | Rate of surviving fishes |
| Examination group | 59.0 | 61.0 | 3.4% | 3.50 | 5.60 | 60.0% | 1921 | 96.1% |
| Control group | 59.0 | 59.5 | 0.8% | 3.50 | 5.23 | 49.4% | 1512 | 75.6% |

Example 18

Growth Promoting Effect of Feed of the Present Invention (Part 2)

A dry substance (one that was taken out from the waste oil of cooking oil for Tenpura that had been used for treatment, to which part of the waste oil adhered) that had been obtained by performing Example 15 was fed to broiler chickens as a part of feed, and the presence or absence of a growth promoting effect was examined.

1. Experimental Conditions

Object: broiler of Cobb

Density in a gauge and number of chickens: each group comprised of 6 gauges (18 chickens), wherein 3 chickens were enclosed in each gauge.

Feed for the examination group: a mixture of corn with the feed that had been obtained in Example 15; crude proteins were 21.1% by weight and calorie was 12.55 MJ/kg.

Feed for the control group: a mixture of corn, soymeal, fishmeal, and corn oil; crude proteins were 21.2% by weight and calorie was 12.55 MJ/kg.

Examination period: from 15 days old to 27 clays old

2. Results

Table 18 shows the results. As is clear from Table 18, in the examination group a somatic growth effect was obtained, of which effect was significantly larger than that of the control group. Namely, it was confirmed that the feed that had been prepared according to the method of the present invention had a large somatic growth effect, as compared to the fishmeal that was produced by a conventional method.

TABLE 18

| | Average weight (g) before start of Examination (15 days old) | Average weight (g) after Examination (27 days old) | Increasing rate (%) of weight |
|---|---|---|---|
| Examination group | 378 ± 48 | 730 ± 119 | 93.1 |
| Control group | 378 ± 49 | 707 ± 77 | 87.0 |

The invention claimed is:

1. A method for reducing water content of an object to be treated, characterized in that the object to be treated contains water or water and an oil-soluble substance, the method com the object to be treated with a oil under an ordinary pressure and at a temperature of 20 to 45 degrees Celsius, wherein an amount of the object to be treated is 60% by weight or lower of an amount of the oil.

2. The method of claim 1, wherein the mixing of the object to be treated with the oil is performed by using a cooling tower, supplying the object to be treated and the oil into a storage tank that is set at a lower part of the cooling tower, and transporting the object to be treated and the oil from the storage tank to an upper part of the cooling tower, and showering down them from the upper part of the cooling tower to the storage tank.

3. The method of claim 1, wherein the mixing of the object to be treated with the oil is performed by installing a submersible pump in a storage tank, impounding the object to be treated and the oil in the storage tank, and spraying a fountain of them by using the submersible pump.

4. The method of claim 1, wherein the mixing of the object to be treated with the oil is performed by bubbling a mixture of the object to be treated and the oil with a gas and/or stirring the mixture, or by shaking or vibrating a container in which the mixture is contained.

5. The method of claim 4, wherein the mixing is performed until substantially no water remains in a treated object.

6. The method according to claim 1, wherein a gas is blown during the mixing so that the gas comes into contact with the mixture of the object to be treated and the oil.

7. The method according to claim 4, wherein the gas is at least one member selected from the group consisting of air, carbon dioxide, and nitrogen.

8. The method according to claim 4, wherein the gas is a dry one having a low water content.

9. The method according to claim 6, wherein the gas that is blown passes through only once on or above the mixture of the object to be treated and the oil.

10. The method according to claim 6, wherein the gas that is blown is used in circle, and wherein the gas that held water by coming into contact with the mixture of the object to be treated and the oil is dried and then used again for blowing.

11. The method according to claim 1, wherein the mixing is performed in the presence of a cationic or anionic surfactant.

12. The method according to claim 1, which is performed in the presence of at least one microorganism selected from the group consisting of various Koji-kin, Phizopus, and Mucor.

13. The method according to claim 1, which is performed in the presence of an antioxidative substance.

14. The method according to claim 1, wherein the object to be treated is at least one member selected from the group consisting of effluents of breweries of alcoholic drinks, activated sludge, an effluent by the production of palm oil, a mixture of livestock excreta, domestic kitchen garbage, a residue by food manufacturing, sea water, and their concentrates.

15. The method according to claim 1, wherein the object to be treated is at least one member selected from the group consisting of hydrous tea-leaf; grinded nut of palm, and grinded nut of camellia.

16. The method according to claim 1, wherein the object to be treated is a dead fish and/or garbage of a fish.

17. A method for producing fuel, which comprises a step (1) for reducing water content of an object to be treated by the method according to claim 1, and a step (2) for molding a mixture of the treated object, of which water content has been reduced, and the oil.

18. A method for producing a dry substance derived from a concentrate of an object to be treated or the object to be treated, which comprises a step (1) for reducing water content of the object to be treated by the method according to claim 1, and a step (2) for separating from the oil the treated object, of which water content has been reduced.

19. The method for producing a dry substance derived from an object to be treated according to claim 18, wherein the step (1) is performed until substantially no water remains in a treated object, and which further comprises, after the step (2), a step (3) for washing the treated object that contains substantially no water and that was obtained by the step (2) with a solvent that can dissolve and clean up the oil, and a step (4) for removing the solvent that was used for washing to obtain the treated object that contains substantially no water.

20. The method for producing a dry substance derived from a concentrate of an object to be treated or the object to be treated according to claim 18, wherein the object to be treated is sea water or a concentrate of it, and the oil is an edible oil and fat.

21. The method for producing a dry substance derived from an object to be treated according to claim 18, which further comprises, after the step (2), a step (3) for compressing the treated object, of which water content has been reduced, to reduce oil content of the treated object.

22. A method for obtaining fresh water from sea water, which comprises (i) mixing the sea water or a concentrate of it with oil at a temperature that is lower than the boiling point of water, at which temperature the oil is liquid, (ii) during the above mixing, blowing a gas so that the gas comes into contact with the mixture of the sea water or the concentrate of it and the oil to make the gas hold the water that is derived from the sea water or the concentrate of it, and (iii) removing water from the gas that has held the water.

23. The method for obtaining fresh water from sea water according to claim 22, wherein the gas is used in circle by blowing to step (ii) the gas, from which water was removed in the step (iii).

24. The method for producing a dry substance derived from an object to be treated according to claim 1, which is a method for producing feed, diet, or fertilizer.

25. A method for producing a dry substance derived from an object to be treated, which comprises, in this order, a step (I) for reducing water content of the object to be treated by mixing the object to be treated containing water or water and the oil-soluble substance with oil at a temperature that is lower than the boiling point of water, at which temperature the oil is liquid, a step (II) for separating from the oil the treated object, of which water content has been reduced, and a step (III) for compressing the treated object, of which water content has been reduced, to reduce oil content of the treated object, and further comprises, after the step (II) or (III), a step (IV) for adding microorganism to the treated object, of which water content has been reduced, and fermenting it to obtain fermented feed, fermented diet, or fermented fertilizer.

* * * * *

UNITED STATES PATENT AND TRADEMARK OFFICE
CERTIFICATE OF CORRECTION

| | |
|---|---|
| PATENT NO. | : 9,138,660 B2 |
| APPLICATION NO. | : 14/119123 |
| DATED | : September 22, 2015 |
| INVENTOR(S) | : Masahiro Yamamoto |

It is certified that error appears in the above-identified patent and that said Letters Patent is hereby corrected as shown below:

In the Claims:

At column 30, claim number 1, line number 25, "1. A method for reducing water content of an object to be treated, characterized in that the object to be treated contains water or water and an oil-soluble substance, the method com the object to be treated with a oil under an ordinary pressure and at a temperature of 20 to 45 degrees Celsius, wherein an amount of the object to be treated is 60% by weight or lower of an amount of the oil." should read -- 1. A method for reducing water content of an object to be treated, characterized in that the object to be treated contains water or water and an oil-soluble substance, the method comprising: mixing the object to be treated with a oil under an ordinary pressure and at a temperature of 20 to 45 degrees Celsius, wherein an amount of the object to be treated is 60% by weight or lower of an amount of the oil. --

Signed and Sealed this
Tenth Day of May, 2016

Michelle K. Lee
*Director of the United States Patent and Trademark Office*